(12) United States Patent
Grimme et al.

(10) Patent No.: US 6,532,065 B1
(45) Date of Patent: Mar. 11, 2003

(54) DEVICE AND METHOD FOR CONTROLLING THE SURFACE OF AN OBJECT

(75) Inventors: Ralf Grimme, Pleidelsheim (DE); Bernhard Klumpp, Fellbach (DE); Michael Hoffmann, Tamins (CH); John David Smith, Cedar Creek, TX (US)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/403,019
(22) PCT Filed: Apr. 15, 1998
(86) PCT No.: PCT/EP98/02195
  § 371 (c)(1),
  (2), (4) Date: Feb. 7, 2000
(87) PCT Pub. No.: WO98/48243
  PCT Pub. Date: Oct. 29, 1998

(30) Foreign Application Priority Data

Apr. 18, 1997 (DE) .......................................... 197 16 264

(51) Int. Cl.[7] .............................................. G01N 21/88
(52) U.S. Cl. .................................................. 356/237.2
(58) Field of Search ........................... 356/237.2, 237.3, 356/237.4, 237.5, 239.7, 239.8

(56) References Cited

U.S. PATENT DOCUMENTS

| 4,342,515 A | * | 8/1982 | Akiba et al. ............. 356/237.3 |
| 4,449,818 A | * | 5/1984 | Yamaguchi et al. ...... 356/237.3 |
| 5,105,149 A | | 4/1992 | Tokura |
| 5,305,079 A | | 4/1994 | Albrecht et al. |
| 5,331,396 A | * | 7/1994 | Yukawa et al. .......... 356/237.8 |
| 5,521,692 A | | 5/1996 | Bares |
| 5,585,916 A | * | 12/1996 | Miura et al. .............. 356/237.4 |

FOREIGN PATENT DOCUMENTS

| DE | 3626724 A1 | 2/1988 |
| DE | 3637477 A1 | 5/1988 |
| DE | 3540288 C2 | 10/1988 |
| DE | 3741616 A1 | 6/1989 |

* cited by examiner

*Primary Examiner*—Richard A. Rosenberger
(74) *Attorney, Agent, or Firm*—Jones, Tullar & Cooper, P.C.

(57) ABSTRACT

The invention relates to a device (1) suitable for controlling a surface (8) of an object (7), notably with respect to raised areas on said surface (8). The device (1) comprises a light source (2, 3) for generating a light beam (5, 6) directed towards the surface as well as a light sensor (4) for detecting light scattered by a raised area on the surface (8). The light beam (5, 6) generated by the light source (2, 3) is configured so as to scan the surface (8) in such a way that the raised area on the surface scatters the light beam (5, 6). If there is no raised area the light beam (5, 6) undergoes ideally no, or else only slight, changes. The light sensor (4) is arranged in such a way that at least part of the scattered light can be detected. In this manner it is possible to detect, for example, impurities on uneven or structured surfaces.

13 Claims, 1 Drawing Sheet

DEVICE AND METHOD FOR CONTROLLING THE SURFACE OF AN OBJECT

FIELD OF THE INVENTION

The present invention relates to a device for testing a surface of an object with regard to raised areas of the surface, having a light source for producing a beam of light associated with the surface and having a light sensor for detecting light scattered by a raised area of the surface. The present invention also relates to a method for testing a surface of an object with regard to raised areas of the surface, in which a light beam associated with the surface is produced and light scattered by a raised area of the surface is detected.

BACKGROUND OF THE INVENTION

It is known to test a surface of an object with regard to raised areas of the surface by virtue of the fact that the surface is obliquely illuminated by a light source and observed by an inspector. In a completely general sense, the raised areas of the surface can be impurities which have been deposited on the surface or can be inhomogeneities contained in the surface itself. With appropriate experience, the testing person can recognize, for example, impurities on the order of magnitude of a few micrometers. Clearly, though, this method is only suitable in a limited fashion for the testing of the object in a series production.

In a method known from semiconductor technology, a light beam produced by a light source is directed onto the surface of a silicon wafer at a steep angle. If an impurity is present there, for example, then the light beam is scattered. The presence of the impurity can be inferred from the scattered light that is detected. However, this method can only be used with the extremely flat and smooth surfaces of a silicon wafer.

If the surface of the object to be tested, however, has uneven areas or if the surface is in fact arbitrarily structured, then the light beam striking the surface will be reflected by these uneven areas. The reflected light is then detected in the same manner as the light scattered by impurities. With the known method, however, a distinction cannot be drawn between whether the light has been reflected or scattered. Therefore in this instance as well, the presence of an impurity cannot be reliably inferred from the detected light.

SUMMARY OF THE INVENTION

The object of the present invention is to provide a device and method of the type mentioned at the beginning with which uneven or arbitrarily structured surfaces of an object can also be tested with regard to impurities.

This object is attained by the present invention with a device of the type mentioned at the beginning, by virtue of the fact that the light beam produced by the light source is aligned as a side light in relation to the surface in such a way that the raised area of the surface causes a scattering of the light beam, whereas otherwise, the light beam undergoes as little change as possible or undergoes only a slight change, and that the light sensor is disposed in such a way that at least a part of the scattered light can be detected. Furthermore, this object is attained by the present invention with a method of the type mentioned beginning by virtue of the fact that the light beam is aligned as a side light in relation to the surface in such a way that the light beam is scattered by a raised area of the surface whereas otherwise, the light beam is changed as little as possible or is changed only slightly, and that at least a part of the scattered light is detected.

The light beam is therefore directed as a side light onto the surface of the object. If an impurity is present there, for example, then the light beam is scattered and at least a part of the scattered light is detected by the light sensor. The scattered light in this connection can also have components that are produced by means of a possibly subsequent reflection and/or refraction and/or diffraction. The fact that the light sensor is receiving light permits the inference to be drawn that there is an impurity on the surface. The same is true when there are a number of impurities. However, if there is no raised area on the surface, then the light beam passes over the surface of the object without being particularly scattered, reflected, or the like. This also results in the fact that the light sensor does not detect any scattered light. The fact that the light sensor is not receiving light permits the inference to be drawn that there is no raised area and in particular, no impurity on the surface.

It is therefore unnecessary for the surface of the object to be extremely smooth or flat. Even if the surface contains uneven areas or an arbitrary structure, this does not lead to a scattering, reflection, or the like of the light beam. Instead of this, the light beam passes over these uneven areas of the structure without being particularly influenced by them.

Consequently, even when there are uneven or structured surfaces, it is possible to reliably detect raised areas and therefore in particular impurities on the surface of the object through the use of a side light. In this connection, the side light is an easy-to-produce light beam which can also be easily used in the series production of the object.

In advantageous embodiments of the present invention, the light beam produced by the light source is aligned approximately parallel to the surface and/or the light beam produced by the light source has an angle of approximately 0° to approximately 10° in relation to the surface, in particular an angle of approximately 1° to approximately 7° in relation to the surface. These embodiments produce a side light that is particularly well-suited on the one hand, to scatter when it strikes against an impurity and on the other hand, to essentially experience no changes otherwise. In particular, with side light embodiments of this kind, uneven areas or structures in the surface to be tested have no particular results with regard to an undesirable scattering, reflection, or the like.

In other advantageous embodiments of the present invention, the light source produces a light beam with approximately parallel light and/or the light beam is slightly divergent. These embodiments produce a side light which is suited to undergoing no changes over a greater length in the event that there are no impurities. Also when there are uneven areas or structures in the surface, essentially no scattering or reflection of the light beam is produced due to the parallel or only slightly divergent light beam.

In an advantageous improvement of the present invention, the light sensor is disposed in a plane that extends approximately perpendicular to the surface and approximately parallel to the light beam. It is particularly useful if the light sensor is disposed approximately in the center above a region that is passed over by the light beam. In this manner, a single light sensor can be used to monitor the entire length over which the light beam passes over the surface. In this improvement, one light sensor is therefore sufficient for testing the surface of the object with regard to impurities.

In another advantageous improvement of the present invention, two or more light sensors are provided, which are disposed three-dimensionally in the space around the surface. It is particularly useful if the light sensors are disposed on the circumference of a cylinder around the light beam. In this manner, it is possible to detect impurities on the surface even better and more reliably. At the same time, this improvement permits the entire method for testing to be accelerated due to the plurality of light sensors.

In another advantageous improvement of the present invention, two or more light sources are provided. It is particularly useful if the light beams of the light sources are aligned approximately parallel to one another and/or if the light beams of the light sources are directed in opposition to one another. In this manner, the light beam can be enlarged with regard to the width with which it passes over the surface to be tested. At the same time, this represents an acceleration of the entire testing method. Furthermore, the fact that the light sources act in opposition to one another results in the better and more reliable detection of impurities on the surface.

Other features, possible uses, and advantages of the present invention ensue from the following description of exemplary embodiments of the present invention which are depicted in the drawing. All of the features described or depicted, alone or in arbitrary combinations, constitute the subject of the present invention, independent of their interrelationship in the claims or their back references and independent of their formulation or depiction in the description or in the drawing.

BRIEF DESCRIPTION OF THE DRAWINGS

The sole FIGURE of the drawing shows an exemplary embodiment of a device according to the present invention for testing a surface of an object.

BRIEF DESCRIPTION OF THE PREFERRED EMBODIMENT

Figure 1:
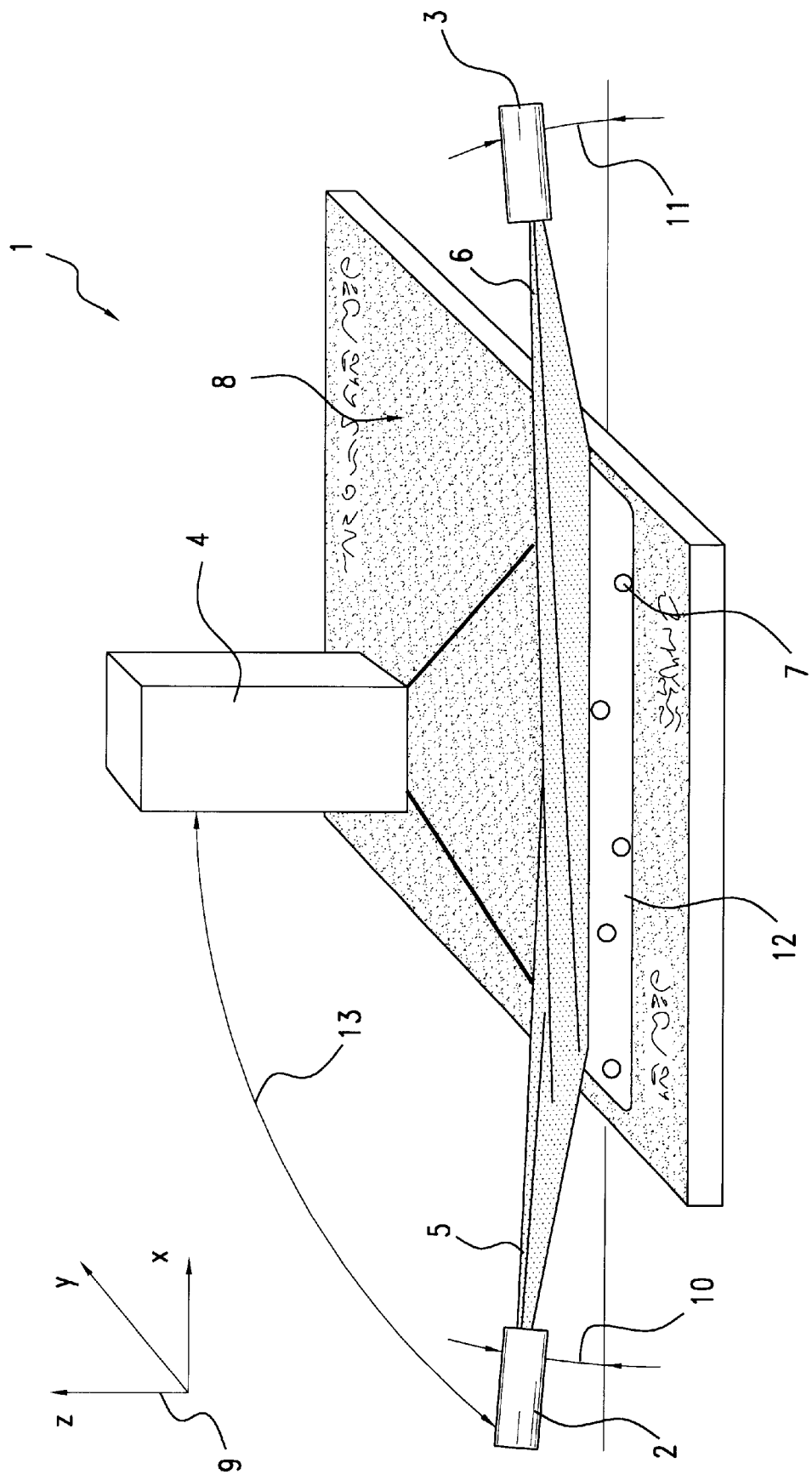

The device 1 shown in the FIGURE has two light sources 2, 3 and a light sensor 4.

The light source 2 produces a light beam 5 and the light source 3 produces a light beam 6. The light beams 5, 6 are comprised of approximately parallel or only slightly divergent light. The light sources 2, 3 can, for example, be laser light sources.

The light sensor 4 is suited for detecting light. If light strikes the light sensor 4, then the correspondingly changed intensity of the light detected by the light sensor 4 is detected. It is immaterial whether this is scattered light, reflected light, or the like. The light sensor 4 can, for example, be a camera with a photosensitive sensor surface.

The light sources 2, 3 and the light sensor 4 are coupled to a computer, not shown, that switches the light sources 2, 3 on and off and processes the intensity of the light detected by the light sensor 4.

An object 7 that has a surface 8 is also shown in the FIGURE. The object 7 can be any object, in particular any technical object, for example a machine, a single component of a machine, a tool for manufacturing a component of this kind, or the like. The surface 8 of the object 7 can be uneven, structured, or in some other way not smooth.

In the FIGURE, the surface 8 constitutes a plane. However, is also possible for the surface 8 to be two-dimensionally or three-dimensionally curved. Furthermore, the surface 8 shown in the FIGURE has a quadrangular shape. However, it is also possible that the surface 8 has an arbitrarily shaped form.

In the FIGURE, a coordinate system 9 is indicated, which has an x-axis and a y-axis in the plane of the surface 8, as well as a z-axis perpendicular to them.

The two light sources 2, 3 are disposed opposite one another on both sides of the surface 8. The two light sources 2, 3 are disposed slightly above the plane of the surface 8. The light beams 5, 6 of the light sources 2, 3 are directed toward the surface 8. The light beams 5, 6 are directed in opposition to each other. The two light beams 5, 6 respectively extend approximately parallel to the x-z plane and are consequently disposed approximately parallel to one another in this respect. However, it is also possible that the two light beams 5, 6 are angled in relation to one another in this respect. In the x-z plane, the two light beams 5, 6 have an angle 10, 11 in relation to the plane of the surface 8. The angle 10, 11 is between approximately 1° and approximately 7°, in particular approximately 6°.

It is likewise possible that the two light beams 5, 6 are disposed approximately parallel to the plane of the surface 8, i.e. that the two angles 10, 11 are approximately equal to 0°. In this instance, it is possible that the two light beams 5, 6 are approximately coaxial.

It is likewise possible that only a single one of the two light sources 2 or 3 is present, whose light beam 5 or 6 is disposed either approximately parallel to the surface 8 or is disposed at the angle 10 or 11 of approximately 6°, for example, in relation to the surface 8.

The two light beams 5, 6 of the light sources 2, 3 represent a side light on the surface 8 of the object 7. This means that the two light beams 5, 6 pass over the surface 8 without particularly touching the surface 8. In particular, the two light beams 5, 6 are essentially not scattered, reflected, or otherwise influenced or changed by the surface 8.

In the FIGURE, a region 12 on the surface 8 over which the two light beams 5, 6 pass is indicated in black. The region 12 has a length in the x direction and a width in the y direction. The length can, for example, be approximately 50 mm, particularly depending on the angle 10, 11 of the light beams 5, 6. The width can, for example, be approximately 3 mm, depending on the light sources 2, 3 used.

The light sensor 4 is disposed above the surface 8 of the object 7 in the z direction. The light sensor 4 is disposed in the x-z plane in which the two light beams 5, 6 extend. Furthermore, the light sensor 4 is disposed approximately in the center above the region 12 constituted by the two light beams 5, 6. The light sensor 4 is aligned in such a way that it can detect light from the direction of the surface 8.

The device 1 described above can be used to test the surface 8 of the object 7 with regard to raised areas of the surface 8. In a completely general sense, a raised area of the surface 8 can be impurities which have been deposited on the surface 8, for example particles, bacteria, drying residues, or the like. In a completely general sense, a raised area of the surface 8 can also be inhomogeneities which are contained in the surface 8 itself, for example inclusions, scratches, convexities, or the like.

In order to test the surface 8 of the object 7, for example with regard to impurities, the two light beams 5, 6 of the two light sources 2, 3 are directed onto the surface 8 in the manner described above. The light sensor 4 is also disposed above the surface 8 in the manner described above.

If there is no impurity in the region 12 of the surface 8, then this results in the fact that the two light beams 5, 6 pass over the surface 8 without any hindrance. The two light beams 5, 6 consequently undergo essentially no change in the region 12. Essentially no scattering, reflection, or the like of the two light beams 5, 6 occurs. As a result, the light sensor 4 detects essentially no change in the detected light. The computer can infer from this that there are no impurities in the region 12 on the surface 8 of the object 7.

However, if there is an impurity in the region 12 of the surface 8, this results in the fact that at least one of the two light beams 5, 6 is scattered by the impurity. Such impurities are represented in the FIGURE as white spots inside the black region 12. The scattered light produced in this manner is deflected in all directions by the impurity. The scattered light in this connection can also have components which are produced by means of a reflection and/or a refraction and/or a diffraction against the impurity and/or subsequently against the surface 8. This results in the fact that at least a part of the scattered light is detected by the light sensor 4. The intensity of the light detected by the light sensor 4 changes as a result of this. The computer can infer from this that there is an impurity inside the region 12 on the surface 8.

For example, the object 7 is then shifted in the plane of the surface 8 by a distance in the y direction that approximately corresponds to the width of the region 12. As a result, the two light beams 5, 6 pass over a new region that adjoins the previous region 12. The testing method described above is then repeated for this new region. In this manner, the entire surface 8 of the object 7 can be successively tested with regard to impurities.

The method described above can be used to test the surface 8 of the object 7 with regard to raised areas of the surface 8. This testing can be carried out within the scope of a quality check, for example of the finish quality of the surface 8, or within the scope of a test or analysis of the material properties of the object 7, or within the scope of a determination as to the number, size, or concentration of particles or the like on the surface 8.

In the FIGURE, the angle between the light sensor 4 and the light beam 5 of the light source 2 is indicated with the reference numeral 13. This angle 13 equals 90° minus the magnitude of the angle 10. However, it is likewise possible that the light sensor 4 is disposed at another angle 13, i.e. is not perpendicular to the plane of the surface 8. Furthermore, the light sensor 4 can also be disposed at an angle in relation to the x-z plane, i.e. oblique to the surface 8 in this regard. It is only essential that the light sensor 4 is disposed in such a way that it can observe the region 12 passed over by the two light beams 5, 6 and that it can detect light coming from there.

It is likewise possible that not only the light sensor 4 is provided, but that a number of light sensors are provided. These can be disposed three-dimensionally in the space above the surface 8. For example, a number of light sensors can be disposed on the circumference of a cylinder whose axis is constituted by the two light beams 5, 6. In particular, this permits material analyses or the like to be carried out.

It is also possible that not only the two light sources 2, 3 are provided, but that a number of light sources are provided. For example, these light sources can be disposed in two rows next to one another above the surface 8. In this manner, it is possible to enlarge the region 12 through an appropriate number of light sources and a corresponding number of light sensors and as a result, to possibly test the entire surface 8 of the object 7 by means of a single testing procedure.

If the surface 8 of the object 7 is arched, then particular parts of the surface 8 which essentially constitute a plane in and of themselves can always be singled out and tested. In this manner, therefore, even an arched surface 8 can be successively tested with regard to impurities.

What is claimed is:

1. A device for testing an object with an uneven or arbitrarily structured surface for impurities in the form of raised areas on the surface, comprising:
    at least one light source for producing at least one light beam comprising approximately parallel light which is directed at the surface of the object and sweeps over a region of the surface of the object; and
    a non-polarizing light sensor disposed in a plane that extends approximately perpendicular to the surface of the object, wherein incident impurities in the region of the surface of the object swept by said approximately parallel light cause a scattering of said at least one light beam, whereas those parts of the region free of incident impurities cause no change, or only a slight change, of said at least one light beam, and wherein at least a part of said at least one light beam scattered out of the region of the surface swept by said approximately parallel light is detectable by said light sensor.

2. The device as defined in claim 1, wherein said at least one light beam is aligned approximately parallel to the surface of the object.

3. The device as defined in claim 1, wherein the angle of incidence of said at least one light beam relative to the surface of the object is approximately 0° to approximately 10°.

4. The device as defined in claim 1, wherein the angle of incidence of said at least one light beam relative to the surface of the object is approximately 1° to approximately 7°.

5. The device as defined in claim 1, wherein said at least one light beam is slightly divergent.

6. The device as defined in claim 1, wherein said light sensor is disposed in a plane that extends approximately parallel to said at least one light beam.

7. The device as defined in claim 1, wherein said light sensor is disposed approximately in the middle of a region of the surface of the object swept by said at least one light beam.

8. The device as defined in claim 1, wherein two light sources are provided.

9. The device as defined in claim 8, wherein the light beams emitted by said two light sources are aligned approximately parallel to one another.

10. The device as defined in claim 8, wherein the light beams emitted by said two light sources are oriented in opposition to one another.

11. A method for testing an object with an uneven or arbitrarily structured surface for impurities in the form of raised areas on the surface, comprising the steps of:
    producing at least one light beam of approximately parallel light;
    directing said at least one light beam at an angle to the surface of the object and sweeping a region of the surface of the object by the at least one light beam;
    disposing at least one non-polarizing light sensor in a plane that extends approximately perpendicular to the surface of the object; and
    detecting, due to the disposition of the at least one non-polarizing light sensor, at least a part of the light from the at least one light beam which is scattered as a result of the at least one light beam sweeping the region of the surface of the object, wherein said scattering is caused by incident impurities in the region swept by the at least one light beam, whereas those parts of the region free of incident impurities cause no change, or only a slight change of the at least one light beam.

12. The method as defined in claim 11, wherein when scattering is detected the inference is drawn that the surface of the object in the region contains impurities.

13. The method as defined in claim 11, wherein when no scattering is detected the inference is drawn that the surface of the object in the region does not contain impurities.

* * * * *

UNITED STATES PATENT AND TRADEMARK OFFICE
CERTIFICATE OF CORRECTION

| | | |
|---|---|---|
| PATENT NO. | : 6,532,065 B1 | Page 1 of 1 |
| APPLICATION NO. | : 09/403019 | |
| DATED | : March 11, 2003 | |
| INVENTOR(S) | : Ralf Grimme et al. | |

It is certified that error appears in the above-identified patent and that said Letters Patent is hereby corrected as shown below:

Title page, item (75), the last two inventors "Michael Hoffmann" and "John David Smith" should be deleted.

Signed and Sealed this
Twenty-seventh Day of March, 2012

David J. Kappos
*Director of the United States Patent and Trademark Office*